(12) United States Patent
Lee et al.

(10) Patent No.: US 8,298,424 B2
(45) Date of Patent: Oct. 30, 2012

(54) APARTMENT-SHAPED ANAEROBIC DIGESTER FOR PRODUCING BIOGAS

(75) Inventors: Sang Bum Lee, Chungcheongbuk-do (KR); Ke Ho Lee, Chungcheongbuk-do (KR)

(73) Assignee: Sang Bum Lee, Chungcheongbuk-do (KR)

( * ) Notice: Subject to any disclaimer, the term of this patent is extended or adjusted under 35 U.S.C. 154(b) by 349 days.

(21) Appl. No.: 12/705,859

(22) Filed: Feb. 15, 2010

(65) Prior Publication Data

US 2010/0206791 A1    Aug. 19, 2010

(30) Foreign Application Priority Data

Feb. 16, 2009  (KR) .................. 10-2009-0012435

(51) Int. Cl.
  *C02F 3/28* (2006.01)
(52) U.S. Cl. .......... 210/603; 210/612; 210/631; 210/97; 210/175; 210/259; 423/237; 423/243.01
(58) Field of Classification Search ................ 210/603, 210/612, 613, 631, 916, 97, 175, 259, 260; 423/237, 243.01
See application file for complete search history.

(56) References Cited

U.S. PATENT DOCUMENTS

| | | | |
|---|---|---|---|
| 4,323,367 A * | 4/1982 | Ghosh ........................ 48/197 A |
| 4,372,856 A * | 2/1983 | Morrison ...................... 210/603 |
| 6,171,499 B1 * | 1/2001 | Bouchalat ..................... 210/603 |
| 7,087,775 B2 | 8/2006 | Lee et al. |
| 7,582,140 B2 | 9/2009 | Silva et al. |
| 8,123,944 B2 * | 2/2012 | Haase et al. ................. 210/605 |
| 2003/0034300 A1 * | 2/2003 | Srinivasan et al. ........... 210/610 |
| 2006/0289356 A1 * | 12/2006 | Burnett et al. ................ 210/603 |

FOREIGN PATENT DOCUMENTS

| | | | |
|---|---|---|---|
| JP | 2004-313929 A | * | 11/2004 |
| KR | 100481326 B1 | | 3/2005 |
| WO | 2007075762 A2 | | 7/2007 |

* cited by examiner

*Primary Examiner* — Fred Prince

(74) *Attorney, Agent, or Firm* — Fredrikson & Byron, P.A.

(57) ABSTRACT

Disclosed herein is an anaerobic digester configured to include input reactors into which livestock wastewater or food waste (hereinafter, 'inflow') is introduced; regions of an anaerobic digestion reactor designed for the inflow passing through an input reactor to perform methane fermentation to produce and transfer biogas simultaneously into the next region; an inlet pipe into which sludge liquid is drawn; an inlet pipe into which activated liquid is drawn; a biogas capturing device; a first heat exchange tube to allow the sludge liquid to perform heat exchange with a new inflow; regions of a subsequent treatment reactor to allow the sludge liquid whose heat exchange is completed to be introduced and to treat gas odor components generated from the sludge liquid; and a liquid-composting reactor in which the emitted sludge whose odor components have been removed is stored.

28 Claims, 13 Drawing Sheets

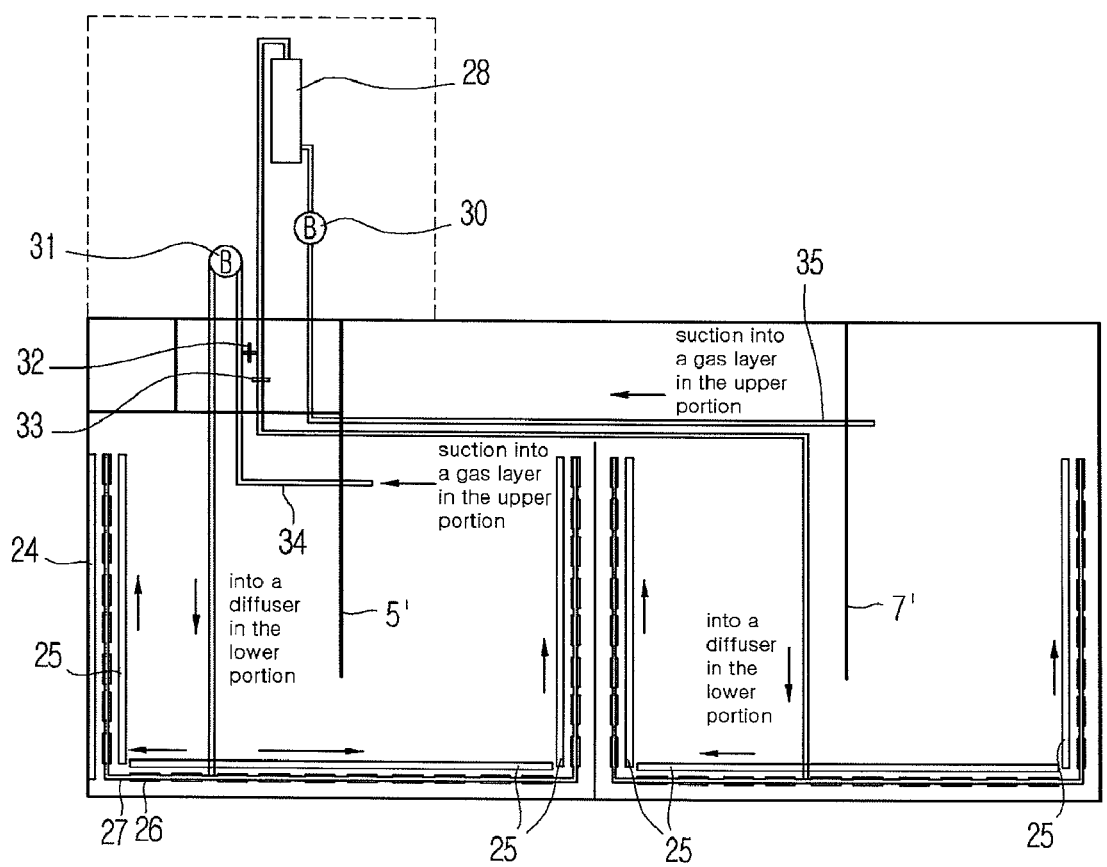

APARTMENT-SHAPED ANAEROBIC DIGESTER FOR PRODUCING BIOGAS

CROSS-REFERENCES TO RELATED APPLICATION

This patent application claims the benefit of priority from Korean Patent Application No. 10-2009-0012435, filed on Feb. 16, 2009, the contents of which are incorporated herein by reference.

BACKGROUND OF THE INVENTION

1. Field of the Invention

The present disclosure relates to an apartment-shaped anaerobic digester for producing biogas.

2. Description of the Related Art

Anaerobic digestion, also known as "methane fermentation", is a biological treatment method for stabilizing organic waste such as food waste, livestock waste, sewage sludge, manure, etc., and a treatment method for hydrolyzing high-molecular organic materials in the presence of facultative and obligate anaerobes under anaerobic conditions, producing volatile fatty acids such as acetic, propionic, butyric acids, etc., and finally gasifying them into methane, hydrogen, carbon dioxide, ammonia, and hydrogen sulfide.

These anaerobic digestions have not been actively used due to widespread adoption of activated sludge methods, but since the mid-1970's oil crisis many studies have been actively conducted on forms of petroleum replacement energy due to their advantages such as availability of recovered gases ($CH_4$ 60-70%, $CO_2$ 30-40%) for fuel, lower power consumption compared to activated sludge methods that require venting large volumes of air, significantly lower biological sludge generation per unit of organic matter compared to aerobic treatment methods, high value as a fertilizer due to the abundance of nitrogen, phosphorus, humus, etc., in the digested sludge, and an environment-friendly resource renewal method for producing fuel and fertilizer in addition to a simple waste decomposition and treatment function.

An anaerobic digestion process is basically divided into the two steps of acid production and methanogenesis. Because microbes in each step are very different in physiological characteristics and nutritional requirements, a balance between two biological groups is offset to inhibit the efficiency of the overall process when external conditions are changed. As an alternative, a two-step fermentation process (two-phase method), which divides a reactor into two reactors for acid production and methanogenesis steps, was suggested. Because acid production and methanogenesis occur simultaneously in a reactor in the traditional first step reaction process (one-phase method), there are limitations in that it is impossible to optimally control the acid production and methanogenesis steps, and stability is not maintained due to its sensitivity to changes in externally-introduced waste. On the contrary, the two-phase method is advantageous in that environmental conditions suitable for each step may be easily maintained, the loading rate into the methane reactor may be appropriately controlled, and inhibition of methane fermentation may be prevented in advance due to its prevention of rapid pH decrease by accumulation of lower fatty acids. However, these two-phase methods are disadvantageous in terms of costs because reactors must be separately provided, thereby requiring a system for transfer from a first reactor to a second reactor, and are complicated in that reaction conditions in each reactor must be separately controlled.

Thus, the present inventors have conducted studies on a novel one-phase method for performing the acid production and methanogenesis steps in one anaerobic digestion reactor instead of the conventional two-phase methods and improving upon the difficulties in simultaneously satisfying optimal conditions for acid production and methanogenesis, which have been identified as problems in conventional one-phase methods, and have developed an apartment-type anaerobic digester for transferring an inflow such as animal manure or food waste within one anaerobic digestion reactor in a first-in and first-out manner and in which optimal conditions may be appropriately provided according to the process flow, thereby leading to completion of the present invention.

SUMMARY OF THE INVENTION

One object of the present invention is to provide an anaerobic digester which is structurally simple and maximizes the production efficiency of biogas by providing optimal anaerobic digestion conditions.

In order to solve the object, the present invention provides an apartment-shaped anaerobic digester, including a first input reactor into which livestock wastewater or food waste (hereinafter, 'inflow') is introduced; a second input reactor into which the inflow passing through the first input reactor is introduced; first, second, third, and fourth regions of an anaerobic digestion reactor designed for the inflow passing through the second input reactor to perform methane fermentation in a first-in and first-out order to produce and transfer biogas simultaneously into the next anaerobic digestion region; a diffusing gas supply tube and a diffuser giving fluidity to the inflow of the first, second, third, and fourth regions; an inlet pipe in a lower layer portion of the fourth region of the anaerobic digestion reactor, into which sludge liquid is drawn in from the lower layer portion; an inlet pipe in an upper layer portion of the forth region of the anaerobic digestion reactor, into which activated liquid is drawn in from the upper layer portion; a biogas capturing device which is connected to a gas layer in the fourth region of the anaerobic digestion reactor; a first heat exchange tube provided inside the first input reactor to allow the sludge liquid drawn in from the inlet pipe in the lower layer portion to perform heat exchange with a new inflow; first, second, third, and fourth regions of a subsequent treatment reactor provided on the upper layer of the anaerobic digestion reactor, to allow the sludge liquid whose heat exchange is completed to be introduced in a first-in and first-out order, and to treat gas odor components generated from the sludge liquid; and a liquid-composting reactor in which an emitted sludge whose odor components have been removed is stored.

Effects

An anaerobic digester according to the present invention does not require a separate gas storage unit and a complex pretreatment when inflow is introduced, may control the temperature of the inflow throughout the entire process using waste heat to provide optimal conditions for growth and development of methanogen, allows for anaerobic digestion of fermentation broth in a first-in and first-out manner to remove factors which may deteriorate the removal efficiency of odor components in the subsequent treatment process when unfermented broth subsequently introduced is first emitted, and may slowly transfer the inflow such that floatation and homogenization of deposits in the inflow may be induced by purification or without purification of self-produced biogas for recycling without a stirrer that is complex and involves high costs. In addition, the present invention may provide an anaerobic digester which is excellent in terms of economy and purity of biogas produced due to the use of a low-cost ammonia and hydrogen sulfide removal device that may prevent a sustained concentration of ammonia and hydrogen sulfide that inhibits the growth and development of methanogen, which has been identified as a disadvantage of conventional gas anaerobic digestion reactors, and can remove 99% or more of ammonia and hydrogen sulfide generated to produce a biogas whose methane content is 80% or more, which is the level of municipal gas, by lowering carbon dioxide content in the biogas to 20% or less.

BRIEF DESCRIPTION OF THE DRAWINGS

The above and other objects, features and other advantages of the present invention will be more clearly understood from the following detailed description taken in conjunction with the accompanying drawings, in which:

FIG. 13 illustrates one embodiment of a diffusing gas partition wall of the present invention in FIG. 4 as observed from above.

DESCRIPTION OF THE PREFERRED EMBODIMENTS

Figure 1:
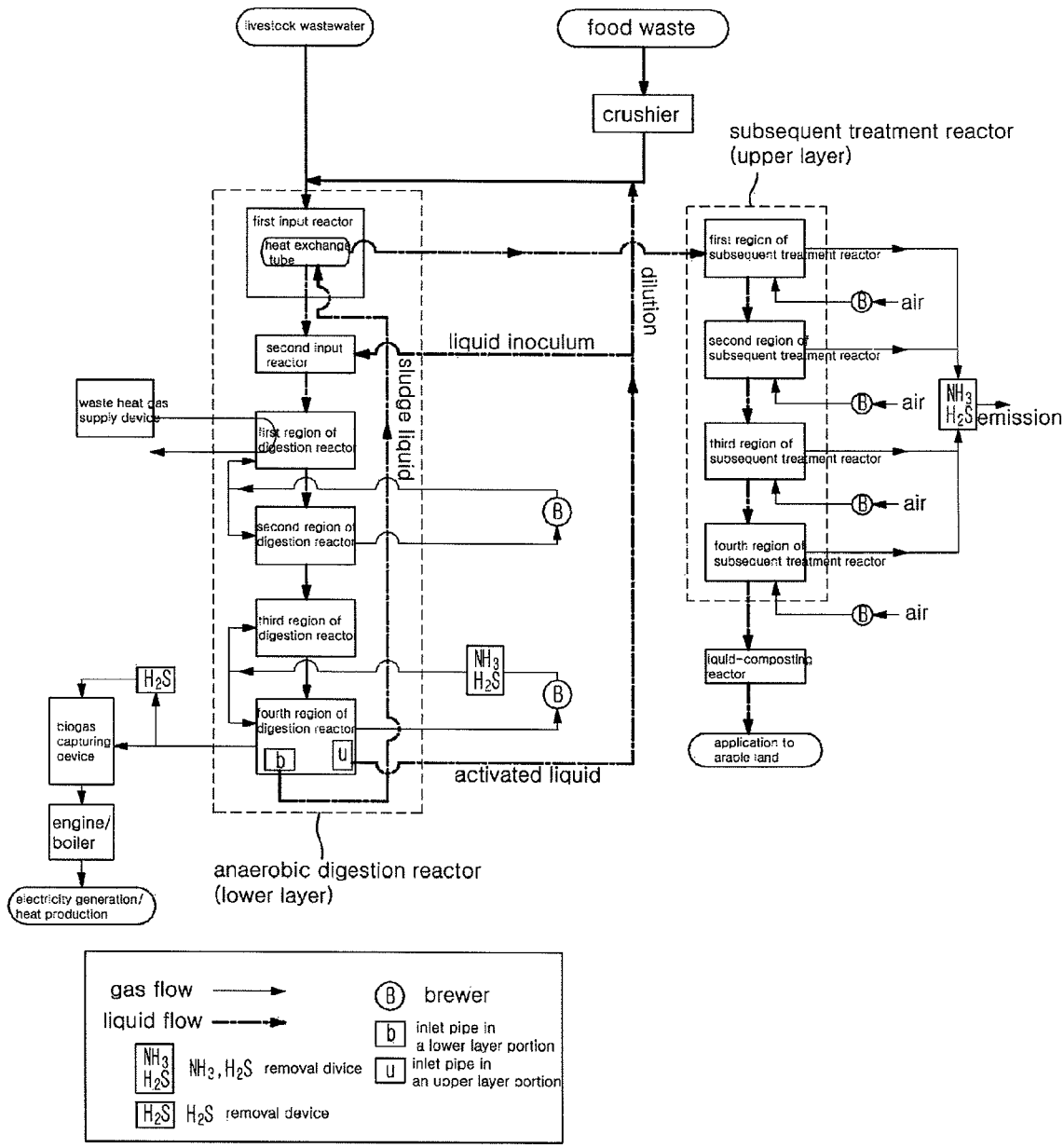
FIG. 1 is a flowchart of a livestock wastewater or food waste treatment process with an apartment-type anaerobic digestion reactor according to the present invention.

Features and advantages of the present invention will be more clearly understood by the following detailed description of the present preferred embodiments by reference to the accompanying drawings. It is first noted that terms or words used herein should be construed as meanings or concepts corresponding to the technical spirit of the present invention, based on the assumption that the inventor has appropriately define the concepts of the terms to best describe the present invention. Also, it should be understood that detailed descriptions of well-known functions and structures related to the present invention are not provided so as not to unnecessarily obscure the essence of the present invention.

The present invention provides an apartment-shaped anaerobic digester which may increase the production efficiency of biogas by providing optimal anaerobic digestion conditions under which acid production and methanogenesis steps may be simultaneously performed in one anaerobic digestion reactor.

Hereinafter, according to one aspect of embodiments of the present invention, an anaerobic digester will be described in detail with reference to the accompanying figures.

According to one aspect of embodiments of the present invention, the anaerobic digester is configured to include:

a first input reactor 3 into which livestock wastewater or food waste (hereinafter, 'inflow') is introduced;

a second input reactor 4 into which the inflow passing through the first input reactor is introduced;

a first region 5, a second region 6, a third region 7, and a fourth region 8 of an anaerobic digestion reactor designed for the inflow passing through the second input reactor 4 to perform methane fermentation in a first-in and first-out order to produce and transfer biogas simultaneously into the next anaerobic digestion region;

a diffusing gas supply tube and a diffuser giving fluidity to the inflow of the first, second, third, and fourth regions;

an inlet pipe 41 in a lower layer portion of the fourth region 8 of the anaerobic digestion reactor, into which sludge liquid is drawn in from the lower layer;

an inlet pipe 42 in an upper layer portion of the forth region of the anaerobic digestion reactor, into which activated liquid is drawn in from the upper layer;

a biogas capturing device which is connected to a gas layer in the fourth region 8 of the anaerobic digestion reactor;

a first heat exchange tube 2 provided inside the first input reactor 3 to allow the sludge liquid drawn in from the inlet pipe 41 in the lower layer portion to perform heat exchange with a new inflow;

a first region 11, a second region 12, a third region 13, and a fourth region 14 of a subsequent treatment reactor provided on the upper layer of the anaerobic digestion reactor, to allow the sludge liquid whose heat exchange has been completed to be introduced in a first-in and first-out order, and to treat gas odor components generated from the sludge liquid; and a liquid-composting reactor in which the emitted sludge whose odor components have been removed is stored.

Figure 2:
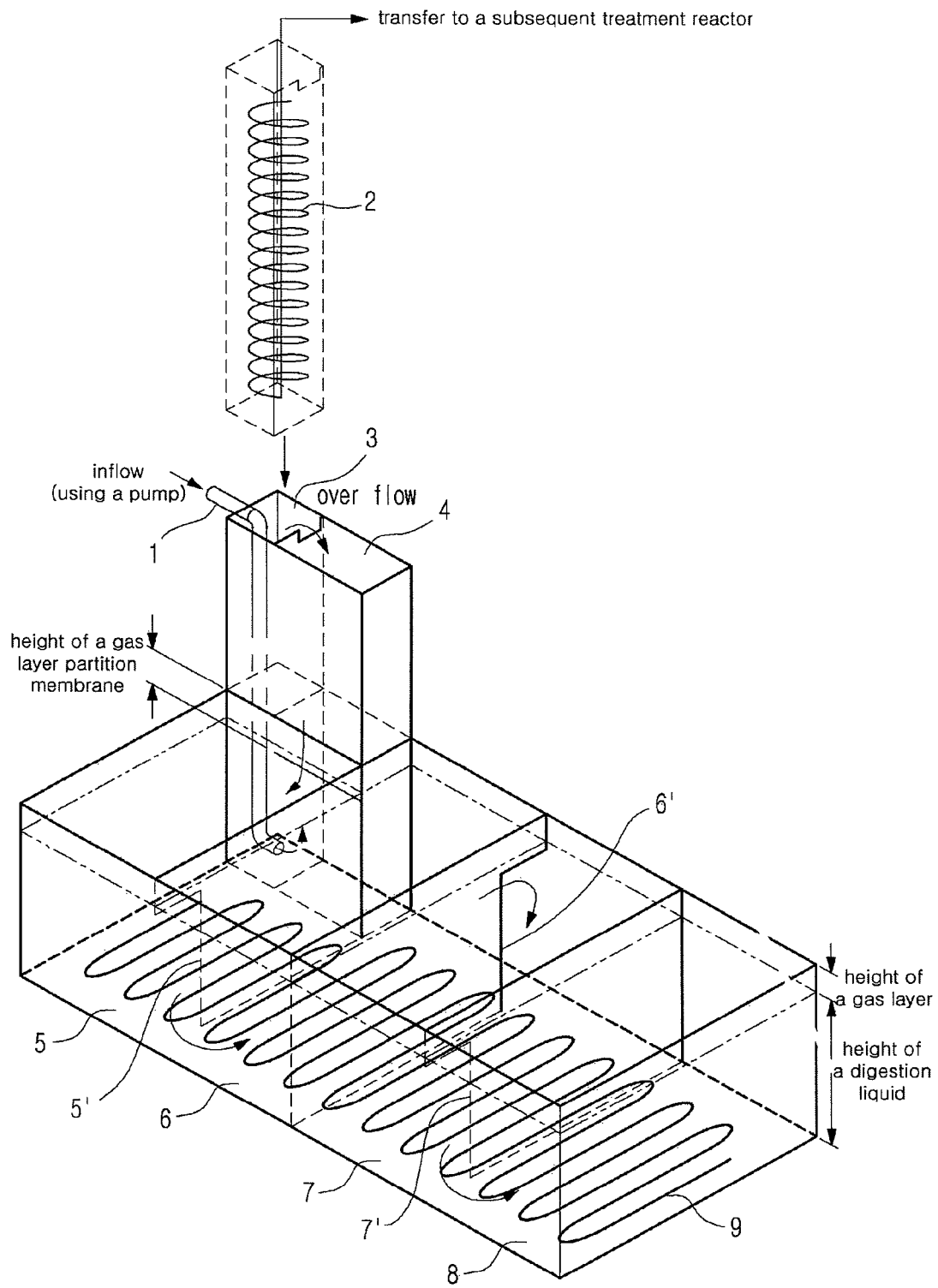
FIG. 2 is a perspective view illustrating a first-floor digestion reactor of an apartment-type anaerobic digestion reactor according to the present invention.

According to one aspect of embodiments of the present invention, an anaerobic digester includes a floor-heating piping 9 on the floors of the first region 5, the second region 6, the third region 7, and the fourth region 8 of the anaerobic digestion reactor to maintain the optimal methane fermentation temperature (See FIG. 2).

The floor-heating piping 9 provides about 35° C. to about 55° C., an optimal temperature range for production of methane by methanogen in the anaerobic digestion reactor. Because the temperatures of initially introduced inflow are about 18° C. in summer and about 8° C. in winter, respectively, the floor-heating piping 9 may minimize a temperature variation between the optimal fermentation temperature for methanogenesis and the temperature of initially introduced inflow.

According to one aspect of embodiments of the present invention, the fifth, sixth, seventh, and eighth regions of the anaerobic digestion reactor of the anaerobic digester are characterized in that they have a structure in which a space for storing biogas produced by methane fermentation is secured between an upper portion of the inflow introduced in each region and a ceiling in each region (See FIG. 2).

When biogas is produced as a result of methane fermentation, the gas produced is stored between a ceiling and an upper portion of the inflow in each region. As a result, the anaerobic digester according to one aspect of embodiments of the present invention requires no separate biogas storage device.

Figure 11:
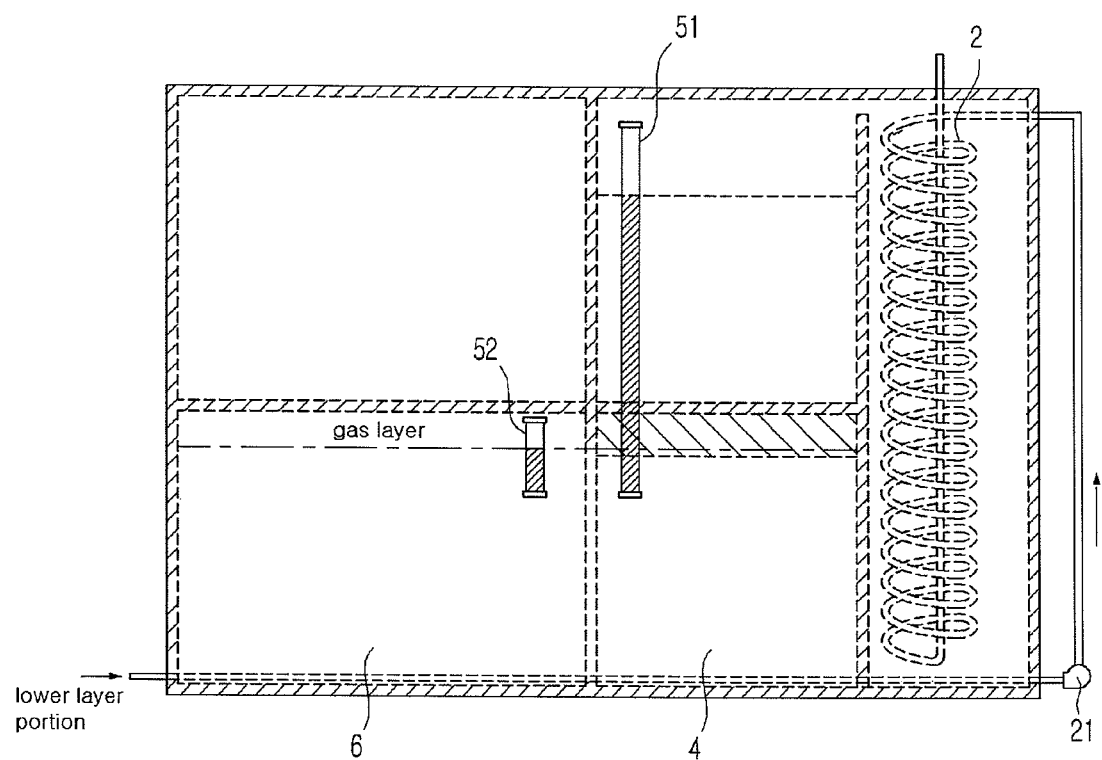
FIG. 11 is a side view of the observation section D in FIG. 4.

In the first region 5 of the anaerobic digestion reactor and the external wall of the second input reactor 4, water level measurement tubes 51 and 52 are provided to measure the levels of inflow in the first region 5 and the second input reactor 4. An inflow level difference may be generated between the first region 5 and the second input reactor 4 by pressure exerted by biogas produced as a result of methane fermentation. That is, when a big pressure is generated in a gas layer of the first region 6 due to a large amount of biogas produced, it is possible to control the time point to stop the input of the inflow because the water level in the second input reactor 4 into which inflow is introduced is increasing (See FIG. 11).

According to one aspect of embodiments of the present invention, the fifth, sixth, seventh, and eighth regions of the anaerobic digestion reactor has a structure in which the regions are divided each other by separation walls 5', 6', and 7'. In this case, the terminal portion of each separation wall 5', 6', and 7' is opened in the form of ']', from the internal wall of the anaerobic digestion reactor except for an upper space in which biogas is stored. The inflow is transferred into the next region through the opened space (See FIG. 2).

In the separation walls 5', 6', and 7' of the anaerobic digestion reactor, the separation wall 5' between the first and second regions and the separation wall 7' between the third and fourth regions are opened in the same direction while the separation wall 6' between the second and third regions has a structure in which the terminal portion is opened in the direction opposite to the openings of the separation wall 5' between the first and second regions and the separation wall 7' between the third and fourth regions. As a result, the inflow is transferred in a zig-zag manner throughout the whole regions of the anaerobic digestion reactor.

The first region 5 of the anaerobic digestion reactor is a region in which acid production is performed, producing pH which is much lower than about 7.2 to about 7.4, an optimal pH range for methanogen. Therefore, control of pH lowered by the inflow to the optimal pH range is required. Such control may be regulated by ammonia components included in a gas introduced by a diffusing gas supply tube 27 and a diffuser 26 which will be below described. As the inflow whose pH is regulated passes through the long distance in a zig-zag manner, pH is controlled within a range appropriate for methane fermentation. That is, the separation membranes 5', 6', and 7' give the buffering capability to the inflow itself by increasing the moving distance of the inflow so that optimal methane fermentation conditions may be provided as the inflow comes closer to the fourth region 8.

Figure 8:
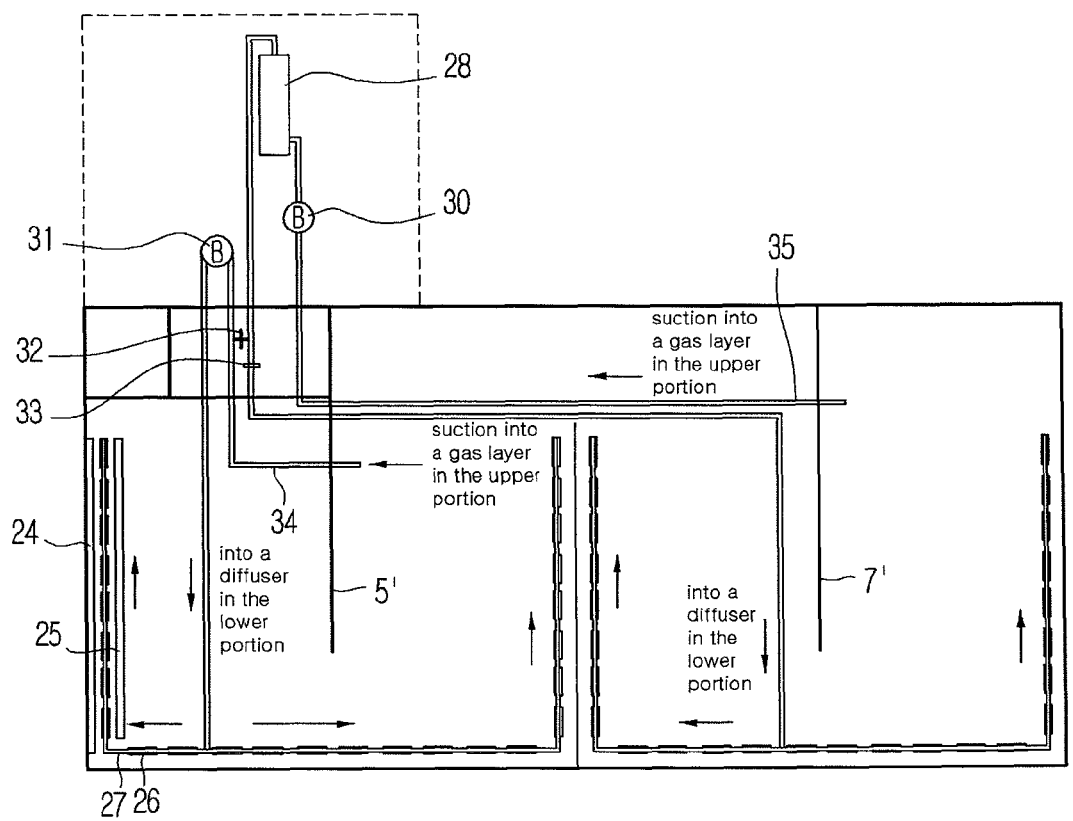
FIG. 8 illustrates observation section D in FIG. 4 as observed from above.

According to one aspect of the present invention, the fifth, sixth, seventh, and eighth regions of the anaerobic digestion reactor each have a structure in which a diffusing gas supply tube 27 and a diffuser 26 giving fluidity to the inflow are installed along the perimeter of the wall on the floor of the other walls except for a wall in the direction where the first input reactor 3 and the second input reactor 4 are installed, the separation wall 5' between the first and second regions, and the separation wall 7' between the third and fourth regions (See FIG. 8).

An anaerobic digestion reactor according to the present invention does not include a separate stirrer. In stead of a stirrer, a gas introduced through the diffusing gas supply tube 27 and the diffuser 26 to provide fluidity to the inflow serves as a stirrer.

Figure 7:
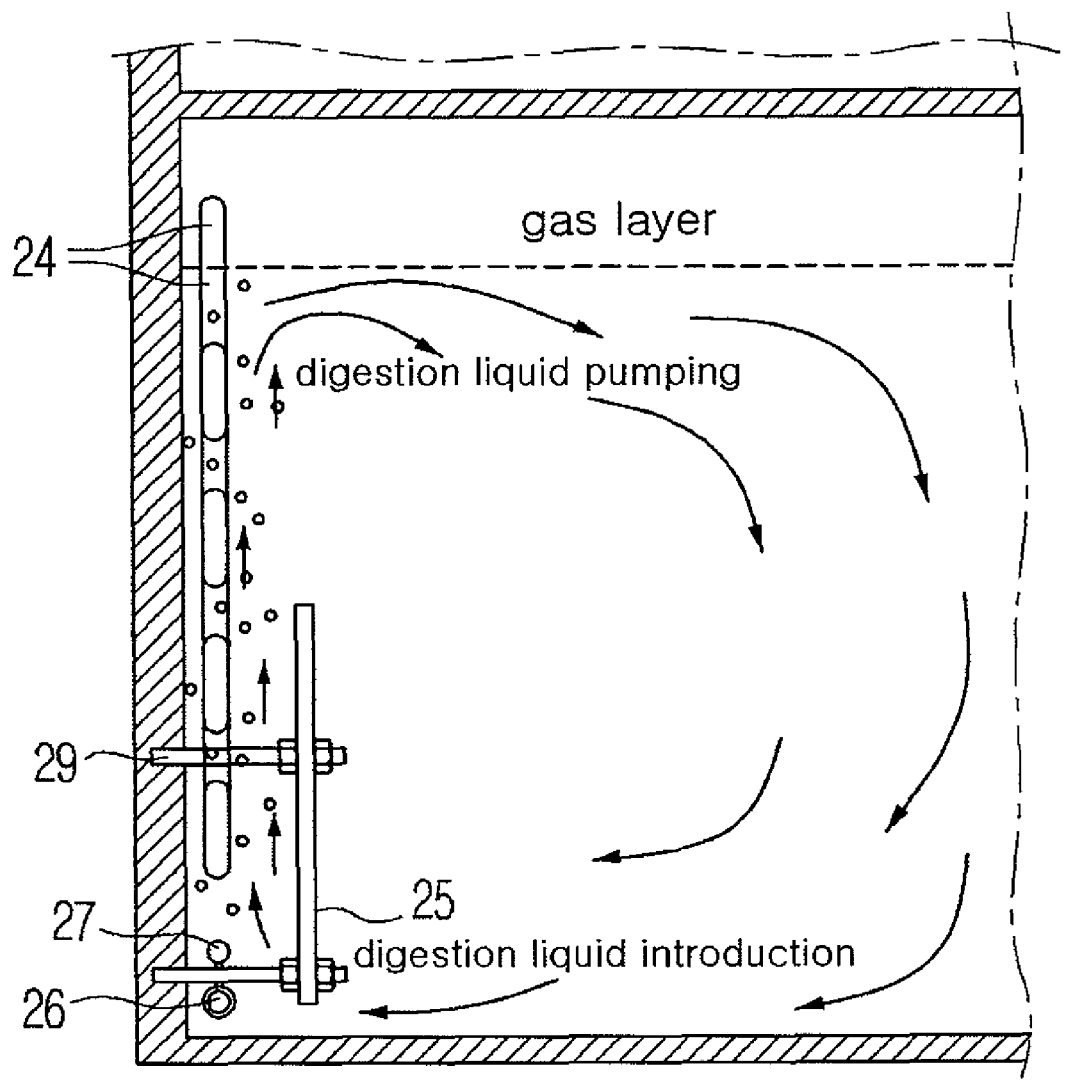
FIG. 7 is a cross-sectional, frontal view of the observation section C in FIG. 4.

In particular, a diffusing gas partition wall 25 in the first region 5 of the anaerobic digestion reactor is installed in front of a second heat exchange tube 24 which will be below described to induce the flow of the diffusing gas introduced from the diffuser 26 installed on the floor of the wall in the vertical direction, and then the diffusing gas passing through the partition wall provides stirring and fluidity to the inflow passing through the first region 5 by giving clockwise rotation to the inflow (See FIG. 7). The diffusing gas introduced may be one which is subjected to a different treatment process in each different region of the anaerobic digestion reactor. This will be more specifically described in the following corresponding part.

Furthermore, a diffusing gas partition wall, installed in an anaerobic digestion reactor according to one embodiment of the present invention may be installed in front of a wall in which a diffusing gas supply tube and a diffuser were installed on the floor from the first region to the fourth region of the anaerobic digestion reactor without being limited to the first region to further give fluidity to the inflow passing through each region (See FIG. 13).

Figure 6:
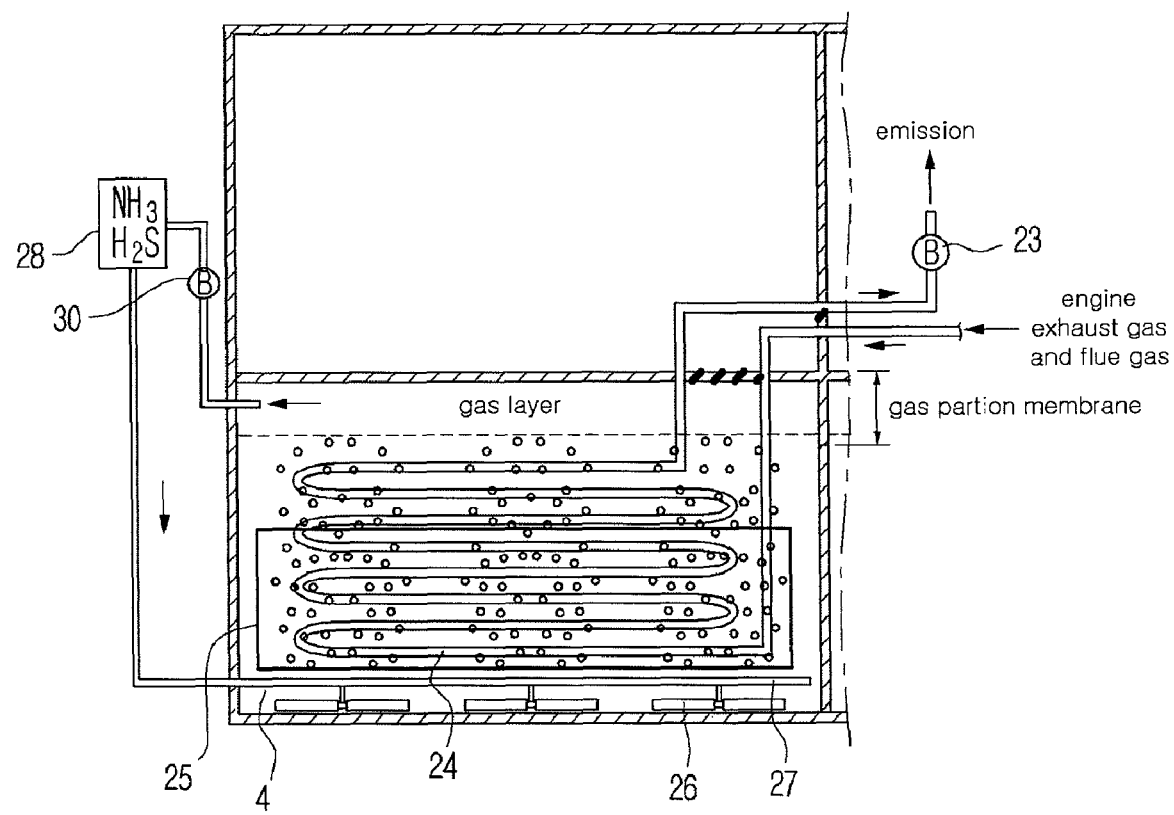
FIG. 6 is a cross-sectional, frontal view of the observation section B in FIG. 4.

According to one aspect of embodiments of the present invention, a second heat exchange tube 24 to exchange heat supplied from an external heat source is provided on the surface of the wall opposite to the separation wall 5' in the first region 5 of the anaerobic digestion reactor for the purpose of minimizing a temperature variation between the temperature of initially introduced inflow and the optimal fermentation temperature for methanogenesis to maximize the methane fermentation efficiency in the second to the forth regions of a subsequent anaerobic digestion reactor (See FIG. 6). The heat supplied from the external source may increase the energy efficiency by using waste heat produced by a boiler flue gas or an engine exhaust gas.

According to one aspect of embodiments of the present invention, the second region 6 of the anaerobic digestion reactor includes a gas piping 34 to recover biogas from the upper gas layer produced as a result of anaerobic digestion through a second suction brewer 31 in the upper gas layer and provide a gas for providing stirring and fluidity to a diffusing gas supply tube 27 and a diffuser 26 which are included in the first region 5 and the second region 6. In addition, a gas piping 35 in the fourth region 8 of the anaerobic digestion reactor is provided to recover biogas from the upper gas layer, produced as a result of the anaerobic digestion through a first suction brewer 30 in the upper gas layer and provide a gas for providing stirring and fluidity to a diffusing gas supply tube 27 and a diffuser 26 which are included in the third region 7 and the fourth region 8 (See FIG. 8).

The biogas drawn in through the gas piping 34 may be not only supplied directly to the first region 5 and the second region 6 without a separate purification of ammonia and hydrogen sulfide, but also supplied in the form of purified ammonia and hydrogen sulfide by manipulating a simple on/off valve of an ammonia and hydrogen sulfide removal device 28 which is selectively connected to an adjacent gas piping 35.

As previously described, the first region 5 of the anaerobic digestion reactor has a relatively low pH environment because an acid production step is performed, and requires a process for maintaining pH appropriate for methane fermentation when the inflow is sequentially transferred to the next region. For this purpose, the present invention may control a lowered pH of the inflow within a pH range appropriate for methane fermentation by introducing intact ammonia included in biogas drawn in through a gas piping 34 of the second region 6 of the anaerobic digestion reactor into a diffusing gas supply tube 27 and a diffuser in the first region without a separate purification process.

Figure 12:
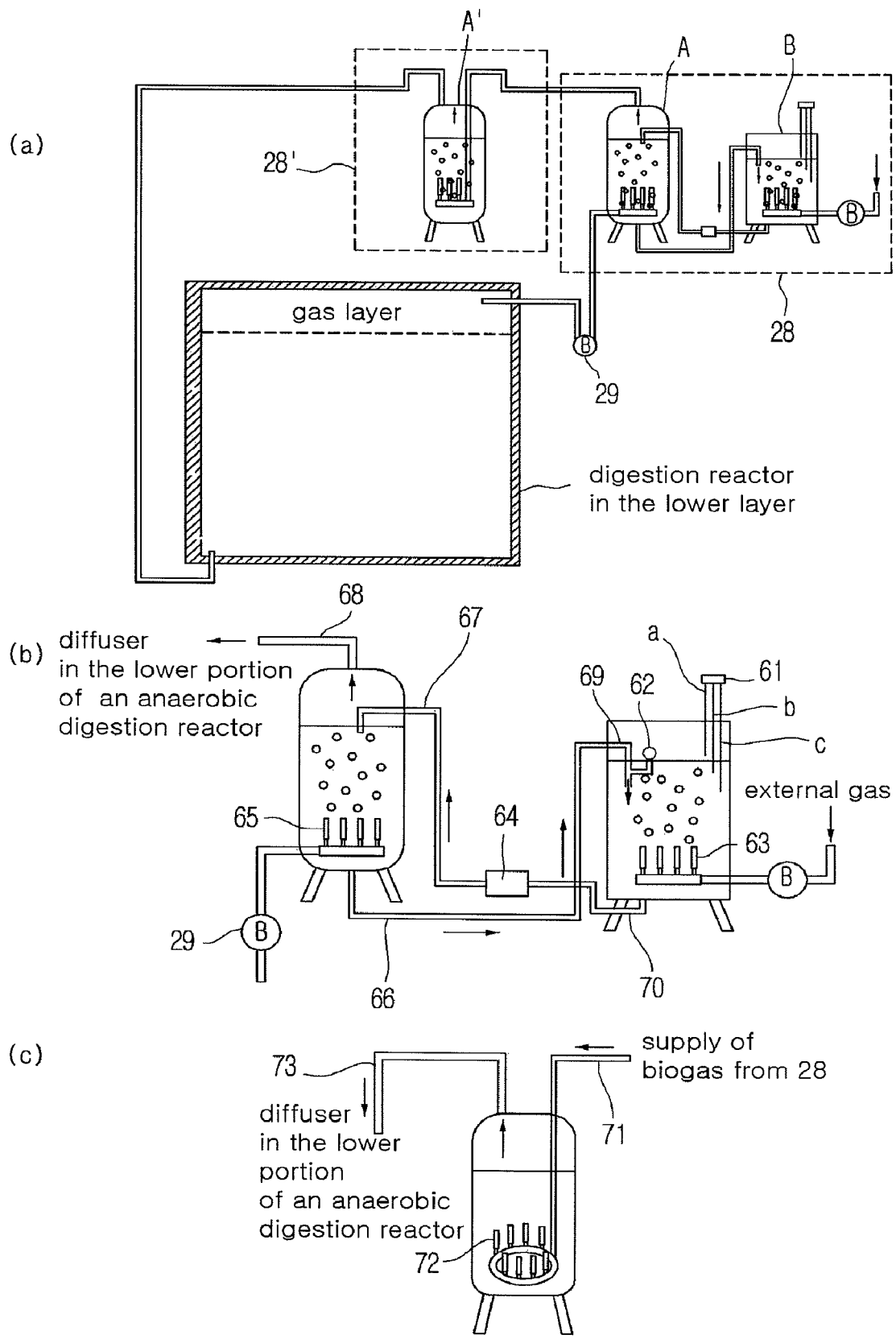
FIG. 12 is a set of drawings illustrating an ammonia/hydrogen sulfide removal device provided in an apartment-shaped anaerobic digestion reactor according to the present invention, showing (a) a schematic connective view of an ammonia/hydrogen sulfide removal device and an anaerobic digestion reactor; (b) an ammonia/hydrogen sulfide removal device in which an A-type tank and a B-type tank are connected; and (c) a hydrogen sulfide removal device in which only an A' type tank is configured.

Because pH of the inflow through the processes in the third region 7 and the fourth region 8 of the anaerobic digestion reactor is controlled at an optimal pH for methane fermentation, a gas for providing stirring and fluidity may be preferably supplied with ammonia removed from the biogas such that these methane fermentation conditions may not be disturbed. Furthermore, the gas may be preferably supplied with even hydrogen sulfide removed from the biogas to increase the purity of a finally produced biogas. For this purpose, it is necessary to remove ammonia and hydrogen sulfide through an ammonia and hydrogen sulfide removal device 28. An ammonia and hydrogen sulfide removal device will be below described in more detail with reference to FIG. 12.

According to one aspect of embodiments of the present invention, an ammonia and hydrogen removal device 28 includes:

a closed-type tank (hereinafter, 'A-type tank') including:
  a diffuser 65 to which a biogas including ammonia and hydrogen sulfide transferred from a gas layer in an anaerobic digestion reactor is supplied;
  water in which the biogas supplied from the diffuser 65 is dissolved;
  a drain pipe 66 through which the water in which the biogas is dissolved is emitted by water level and gas pressure in a lower portion;
  an inlet pipe 67 through which water in which the ammonia and hydrogen sulfide is removed is introduced into an upper portion; and
  an exhaust pipe 68 through which the gas with the ammonia and hydrogen sulfide removed is returned to the anaerobic digestion reactor; and
an open-type tank (hereinafter, 'B-type tank') which includes a *Thiocapsa roseopersicina* culture including:
  a water pipe 69 through which the water drained from a lower portion of the A-type tank is introduced in an upper portion;
  a ball tap for water level control 62 connected to and supported by the water pipe 69;
  a level sensor 61 which senses water level;
  a diffuser 63 to which external air is supplied;
  a drain pipe 70, through which water with ammonia and hydrogen sulfide removed is drained in a lower portion; and
  a drain pump 64 which is connected to the drain pipe 70 and performs an on/off function according to a water level sensing information of the level sensor,
wherein the A-type tank is connected each other to the B-type tank.

According to one aspect of embodiments of the present invention, the A-type tank of the ammonia and hydrogen sulfide removal device 28 supplies ammonia and hydrogen sulfide dissolved in water to the B-type tank, in which the ammonia and hydrogen sulfide are reacted with oxygen supplied from the external air, and removes the ammonia and hydrogen sulfide in the form of ammonium sulfate ($(NH_4)_2SO_4$) as indicated in the following Formula 1.

$$2NH_3 + H_2S + 2O_2 \rightarrow (NH_4)_2SO_4 \quad \text{[Formula 1]}$$

The A-type tank of the removal device 28 is a closed-type one. The tank may preferably maintain an appropriate internal pressure and water level such that water in which the gas introduced from a gas layer of the anaerobic digestion reactor is dissolved may be supplied to the B-type tank and that the internal pressure may be maintained more preferably at about 0.4 kg/cm² to about 0.6 kg/cm².

According to one aspect of embodiments of the present invention, the A-type and B-type tanks of the ammonia and hydrogen sulfide removal device 28 may preferably include a *Thiocapsa roseopersicina* culture. As indicated in the following Formula 2, some enzymes in the *Thiocapsa roseopersicina* culture may convert carbon dioxide and hydrogen sulfide in the biogas into the forms of formaldehyde ($CH_2O$) and sulfuric acid ($H_2SO_4$) salt to increase the purity of the biogas. It is thought that the converted sulfuric acid is additionally reacted with ammonia to be converted into the form of ammonium sulfate as indicated in the following Formula 3.

$$2CO_2 + H_2S + 2H_2O \rightarrow 2(CH_2O) + H_2SO_4 \quad \text{[Formula 2]}$$

$$H_2SO_4 + 2NH_3 \rightarrow (NH_4)_2SO_4 \quad \text{[Formula 3]}$$

As a result of the reaction, hydrogen sulfide included in the biogas may be additionally decreased with some carbon dioxide. In particular, in the conditions under which ammonia and hydrogen sulfide are not removed, the accumulation of ammonia and hydrogen sulfide in a conventional gas stirring type anaerobic digestion reactor in which anaerobic digestion liquid is stirred has been identified as a factor which has adverse effects on biogas production environments (growth and development of methanogen). However, according to the removal device of the present invention, a gas with hydrogen sulfide and ammonia removed, that is, a purified biogas in the upper layer portion may be used for the stirring of the anaerobic digestion liquid, and as a result, carbon dioxide and hydrogen may be supplied as a substrate for methanogenesis to methanogen in the anaerobic digestion liquid. This means that carbon dioxide as an impurity may be combined with extra hydrogen to lead to a decrease in methane concentration and an increase in carbon dioxide concentration in a total biogas produced and as a result, the purity of the biogas may be increased.

When the concentration of hydrogen sulfide introduced into the ammonia and hydrogen sulfide removal device is high, the hydrogen sulfide may be converted into the form of pure sulfur (S) at a rapid rate and removed. That is, when the concentration of hydrogen sulfide is high, the oxidation of hydrogen sulfide ($H_2S$) into sulfur (S) by *Thiocapsa roseopersicina* proceeds relatively more rapidly than that of sulfur (S) into sulfate anion ($SO_4^{2-}$), and thus a large amount of sulfur is accumulated in solution in the removal device and some is precipitated and suspended on the surface of a container or in solution.

Furthermore, the B-type tank of the ammonia and hydrogen sulfide removal device 28 may be preferably supplied with oxygen dissolved in water from the external air. Through the supply, oxygen input not only into the biogas in which ammonia and hydrogen sulfide are to be removed, but also into an anaerobic digestion reactor requiring extreme anaerobic conditions will be blocked in advance.

According to one aspect of embodiments of the present invention, the level sensor 61 in the B-type tank of the ammonia and hydrogen sulfide removal device 28 includes three sensor rods a, b, and c which are different each other in length. When the water level of the B-type tank touches the shortest sensor rod a, a drain pump 64 is operated to supply water with ammonia and hydrogen sulfide removed to the A-type tank. When the water level of the B-type tank touches the middle-length sensor rod b, the drain pump 64 stops its operation. A removal reaction of ammonia and hydrogen sulfide is continuously performed without any supply of gas-phase oxygen to the A-type tank while the solution is circulating in the A-type and B-type tanks.

According to one aspect of embodiments of the present invention, an ammonia and hydrogen sulfide removal device 28 transfers a dissolved biogas with ammonia and hydrogen sulfide removed through the B-type tank to the A-type tank and supplies the biogas through an exhaust pipe in the upper portion of the A-type tank to a diffusing gas supply tube 27 and a diffuser 26 in the lower portion of the anaerobic digestion reactor. More specifically, ammonia ($NH_4$) and hydrogen sulfide ($H_2S$), gasses which are easily dissolved in water, in the biogas which has been transferred to the A-type tank has been dissolved in water while methane ($CH_4$), hydrogen (H), some of carbon dioxide ($CO_2$) are emitted through an exhaust pipe in the upper portion of the A-type tank and supplied to a diffusing gas supply tube 27 and a diffuser 26 in the lower portion of the A-type tank of the present invention. Water in the A-type tank is supplied to the B-type tank while a reaction represented by $2CO_2+H_2S+2H_2O \rightarrow 2(CH_2O)+H_2SO_4$ is performed. As described above in the B-type tank, the rate of oxidation by purple bacteria (*Thiocapsa roseopersicina*) of $H_2S$ groups into S proceeds faster than that of oxidation of S into $SO_4^{2-}$, and thus the application of a transient mass accumulation of S leads to conversion of S groups into $SO_4^{-2}$ by dissolved oxygen which has been supplied to the B-type tank. The binding of $SO_4^{-2}$ with dissolved $NH_4^-$ leads to a fast reaction of ammonia into the form of ammonium sulfate (See Reaction Formula 3). That is, these reactions continuously occur while water is circulating between the A-type tank and the B-type tank.

According to one aspect of embodiments of the present invention, the B-type tank of the ammonia and hydrogen sulfide removal device 28 may be used without liquid phase replacement for about 6 months to about 1 year only by replenishing evaporated moisture. The liquid phase replacement time of the removal device 28 depends on the saturated concentration of ammonium sulfate as a produced material, and the liquid phase may be preferably replaced in terms of removal efficiency when the saturated concentration of the solution in the removal device reaches about 40%.

According to one aspect of embodiments of the present invention, a separate hydrogen sulfide removal device 28' may be additionally connected to the ammonia and hydrogen sulfide removal device 28 in order to increase the removal efficiency of hydrogen sulfide in the ammonia and hydrogen sulfide removal device 28.

One preferable aspect of embodiments of the hydrogen sulfide removal device 28' may be provided in the form of a closed-type tank, including: an inlet pipe 71 into which a biogas with some hydrogen sulfide removed is introduced through a removal device 28; a diffuser 72 which diffuses the biogas introduced from the inlet pipe 71; water including iron hydroxide (II) or iron hydroxide (III) reacting with hydrogen sulfide in the biogas supplied from the diffuser 72; and an exhaust pipe 73 which emits a biogas with hydrogen sulfide removed.

Specifically, 99% or more of ammonia supplied through the exhaust pipe 68 in the upper portion of the A-type tank and the biogas with some hydrogen sulfide removed are dissolved through the diffuser 65 and iron hydroxide (II) or iron hydroxide (III) included in the removal device 28' is reacted with a residual hydrogen sulfide to remove the residual hydrogen sulfide in the form of iron sulfide and water. The hydrogen sulfide removal device 28' may be serially connected to the A-type tank of the ammonia and hydrogen sulfide removal device 28.

More preferably, iron hydroxide (II) or iron hydroxide (III) prepared by a method for preparing mineral hydroxide described in 'Method for preparation of organic chelate' (KR patent No. 0481326 and U.S. Pat. No. 7,087,775) filed by and granted to the present inventors may be used.

The iron sulfide (II) or iron sulfide (III) in the present invention is a material in the form of $Fe(OH)_2$ or $Fe(OH)_3$ obtained by equivalent reaction of conventional bivalent or trivalent iron such as $FeCl_2$, $FeCl_3$, etc., with NaOH in an aqueous solution. A product obtained as in the following Formula 4 may be centrifuged and NaCl may be removed to yield the $Fe(OH)_2$ or $Fe(OH)_3$.

$$FeCl_2+2NaOH \rightarrow Fe(OH)_2+2\beta NaCl$$

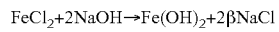

$$FeCl_3+3NaOH \rightarrow Fe(OH)_3+3NaCl \quad \text{[Formula 4]}$$

Because the iron hydroxide (II) or iron hydroxide (III) is fully reacted with hydrogen sulfide, a gas component dissolved into a solution removal system in a removal device by a diffuser in a reaction tank of the present invention, the removal efficiency depends on the gas dissolution capability of the diffuser. The present invention is much more excellent than a method for venting air under high pressure into a conventional desulfurization device and performing an adsorption reaction of FeO(OH) as an iron hydroxide (III) and $Fe_2O_3$ as an iron oxide (III) with a gas-phase hydrogen sulfide to remove the hydrogen sulfide in terms of air venting rate (gas processing capability). In terms of reaction efficiency, the present invention is also much better than conventional desulfurization devices which depend on purity of iron hydroxide (III) and surface area of pellet.

Specifically, a conventional desulfurization device ("The Study of Biogas Production and Energy Use by High-rate Two Phase Anaerobic Treatment of Swine Wastewater (Final report)", p. 151, September, 2006, Department of Industry and Resources, Korea) may adsorb 130 g of hydrogen sulfide per kg of $Fe_2O_3$, while a removal device according to the present invention may adsorb about 478 g of hydrogen sulfide per kg of $Fe(OH)_3$, indicating that the present invention is much better than the conventional device by about 3.7 fold in terms of removal efficiency. Because the present invention has an air venting rate of about 4 $Nm^3$/min, a much better value than 2.5 $Nm^3$/min of the conventional desulfurization device in terms of gas processing, the present invention is also considered to be excellent in processing capability.

As described above, an ammonia and hydrogen sulfide removal device 28 according to the present invention may significantly decrease carbon dioxide content in biogas because an enzyme produced in a *Thiocapsa roseopersicina* culture included therein consumes carbon dioxide during the removal of hydrogen sulfide. Biogas produced in a conventional anaerobic digestion reactor for producing biogas contains only 60% to 70% or less of methane and 35% to 45% or less of carbon dioxide.

On the contrary, when the removal device 28 and/or removal device 28' according to the present invention is used, the removal device 28' may be independently applied for the purpose of removing hydrogen sulfide from a biogas produced by an anaerobic digestion reactor. Furthermore, when the removal device 28 is combined with the removal device 28' for use, optimal anaerobic digestion conditions (prevention of ammonia and hydrogen sulfide accumulation in digestion liquid) may be maintained by supplying a high-purity biogas to an aerobic digestion reactor as a gas for stirring the anaerobic digestion liquid and carbon dioxide content may be decreased to 20% or less, thus leading to an increase in methane content in a total biogas produced to 80% or more by performing a reaction of $2CO_2 + H_2S + 2H_2O \rightarrow 2(CH_2O) + H_2SO_4$ and supplying residual carbon dioxide and hydrogen as a substrate for methanogen in the digestion liquid to convert carbon dioxide as an impurity into methane. Methanogen species and available substrates are summarized in the following Table 1.

TABLE 1

| Methanogen species | Available substrate |
| --- | --- |
| *Methanobacterium, thermoautotrophicum* | $H_2 + CO_2$, CO |
| *Methanobrevibacter arboriphilus* | $H_2 + CO_2$ |
| *Methanococcus vanniellii* | $H_2 + CO_2$, HCOOH |
| *Methanospirillum hungatei* | $H_2 + CO_2$, HCOOH |
| *Methanosarcina barkeri* | $H_2 + CO_2$, $CH_3OH$, $CH_3COOH$, methylamines |
| *Methanosarcina mazei* | $CH_3OH$, $CH_3COOH$, methylamines |
| *Methanothrix soehngenii* | $CH_3COOH$ |
| *Methanolobus tindarius* | $CH_3COOH$, methylamines |
| *Methanococcoides methylutens* | $CH_3COOH$, methylamines |
| *Methanoplanus limicola* | $H_2 + CO_2$, HCOOH |

Because the removal efficiency by the removal device depends on the solubility of a gas to be removed which is transferred to a removal device, it is desirable to increase the gas input rate slowly into the removal device in order to increase the solubility. A better removal efficiency may be achieved in terms of purity increase by increasing the circulation frequency of the gas to be removed in the removal device.

Figure 5:
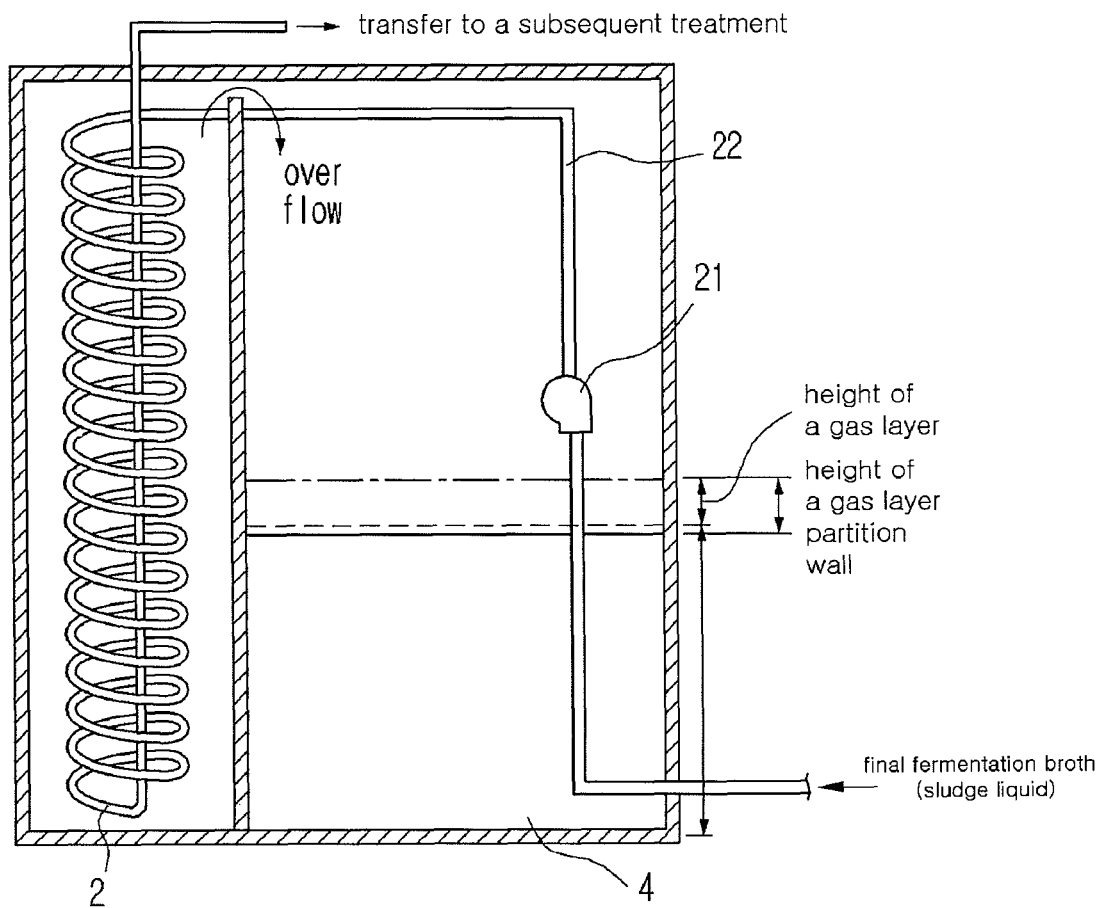
FIG. 5 is a cross-sectional, frontal view of observation section A in FIG. 4.
Figure 9:
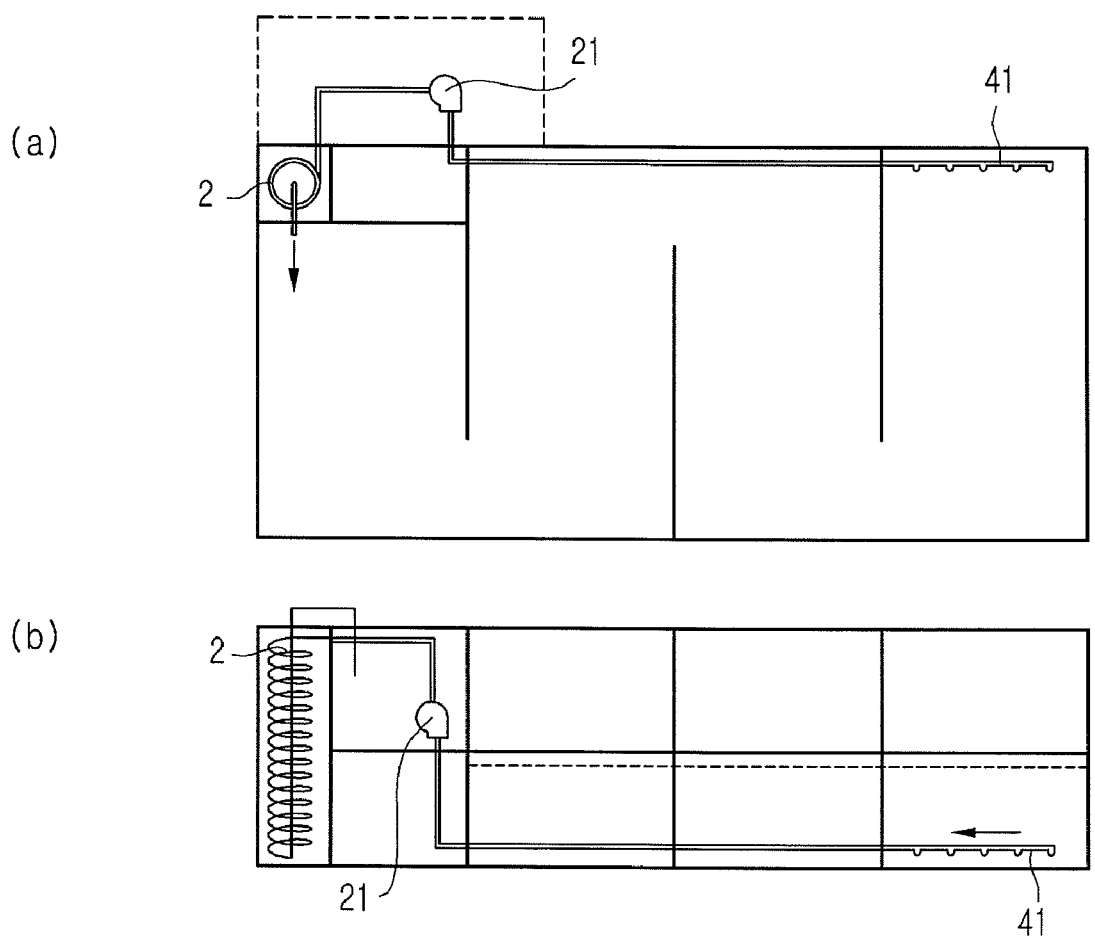
FIG. 9 illustrates (a) a top view and (b) a side view of the arrangement of a pipe that draws in the final fermentation broth in the lower portion of an apartment-shaped anaerobic digestion reactor according to the present invention.

According to one aspect of embodiments of the present invention, a first input reactor 3 in the anaerobic digestion reactor includes a first heat exchange tube 2. Because a sludge pump 21 may be used to introduce a final fermentation broth (sludge liquid) in the lower portion of the fourth region 8 in which the final anaerobic digestion is completed into an inlet pipe 41, installed on the floor of the fourth region 8, transfer it to a first heat exchange tube 2, and circulate it in the first input reactor 3, a new cold inflow may be warmed (See FIGS. 5 and 9).

As described above, because the temperature of an inflow introduced into the anaerobic digestion reactor is about 18° C. in summer and about 8° C. in winter, a significant temperature variation occurs compared to 35° C. to 42° C., a temperature range for mesophilic temperature anaerobic digestion.

The temperature of a final fermentation broth (sludge liquid) in which a final anaerobic digestion is completed becomes about 35° C. Because heat corresponding to the temperature is recovered to the inflow as waste heat, the final fermentation broth is transferred to a subsequent treatment reactor on the upper layer of the anaerobic digestion reactor, and the fermentation step has been completed, no additional temperature control is necessary.

Therefore, the present invention may allow a new inflow to minimize a variation between the temperatures of an actual methane fermentation and an optimal methane fermentation by introducing a first heat exchange pipe 2 connected to an inlet pipe 41 in the lower portion as above to provide a waste heat generated from a relatively high temperature final fermentation broth to the new inflow in a relatively low temperature first input reactor 3.

Figure 10:
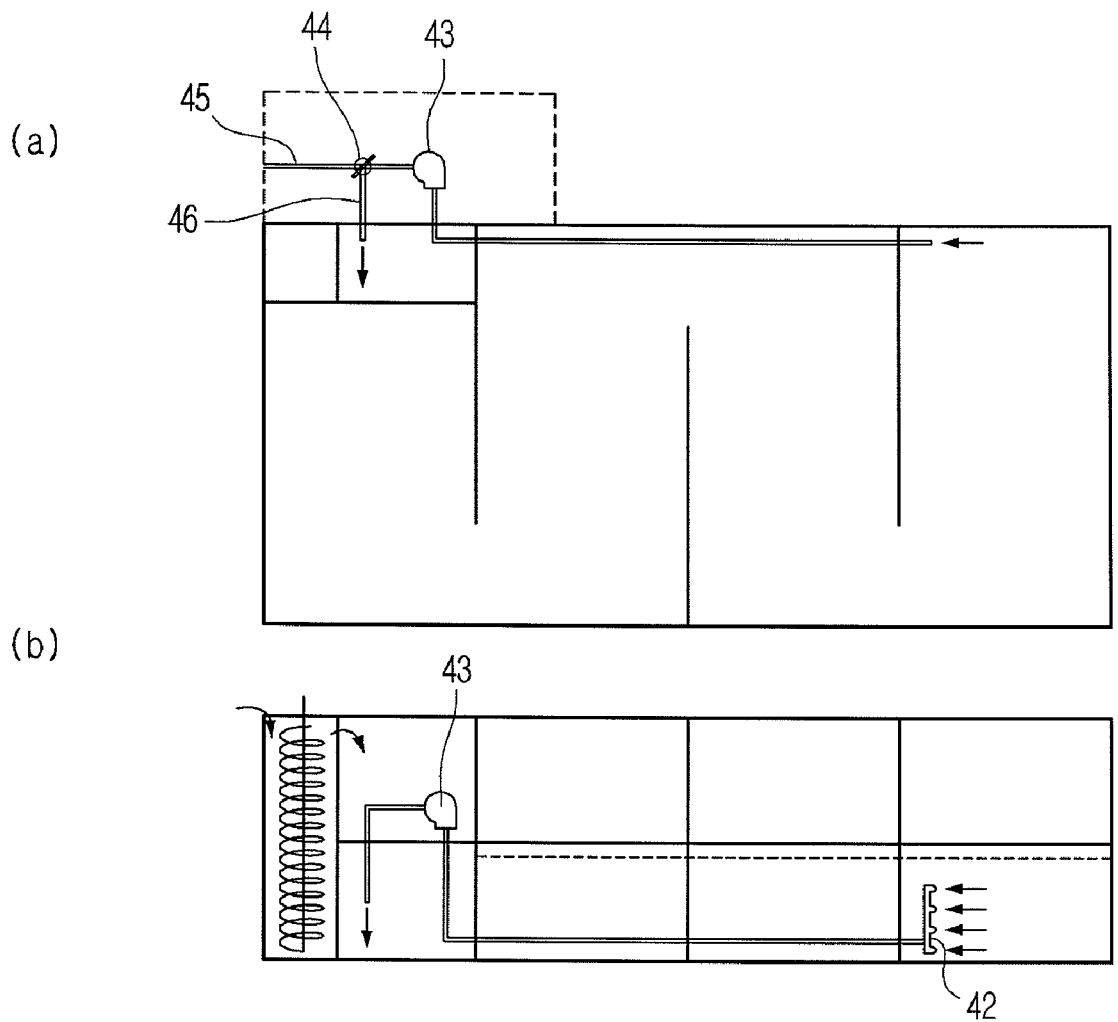
FIG. 10 illustrates (a) a top view and (b) a side view of the arrangement of a pipe that draws in a liquid inoculum and a diluent in the upper layer portion of an apartment-shaped anaerobic digestion reactor according to the present invention.

According to one aspect of embodiments of the present invention, the fourth region 8 of the anaerobic digestion reactor includes an inlet pipe 42 in the upper portion, which draws in an activated liquid in the upper portion. The activated liquid is drawn in through a sludge pump 43. The activated liquid is used as a liquid inoculum when an inflow is a livestock wastewater, while the liquid is used for dilution according to the concentrations of the inflow when the inflow is a food waste. When it is used as a liquid inoculum, it may be introduced into a second input reactor 4 by manipulating a simple on/off valve 44 (See FIG. 10).

According to one aspect of embodiments of the present invention, the anaerobic digestion reactor may further include a hydrogen sulfide removal device between a biogas layer in an upper portion of the fourth region 8 and a biogas capturing device connected thereto in order to increase the removal efficiency of hydrogen sulfide (See FIG. 1). The hydrogen sulfide removal device may use a hydrogen sulfide removal device 28' as mentioned in FIG. 12 (*c*).

Figure 3:
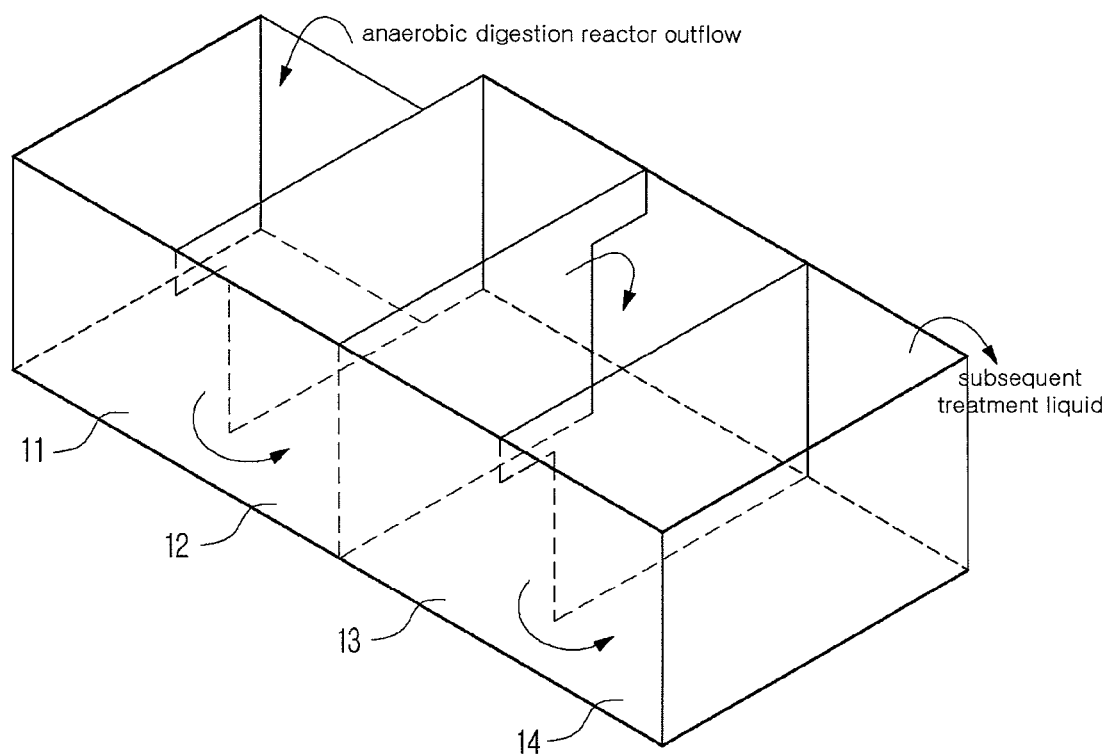
FIG. 3 is a perspective view illustrating a second-floor subsequent treatment reactor of an apartment-type anaerobic digestion reactor according to the present invention.
Figure 4:
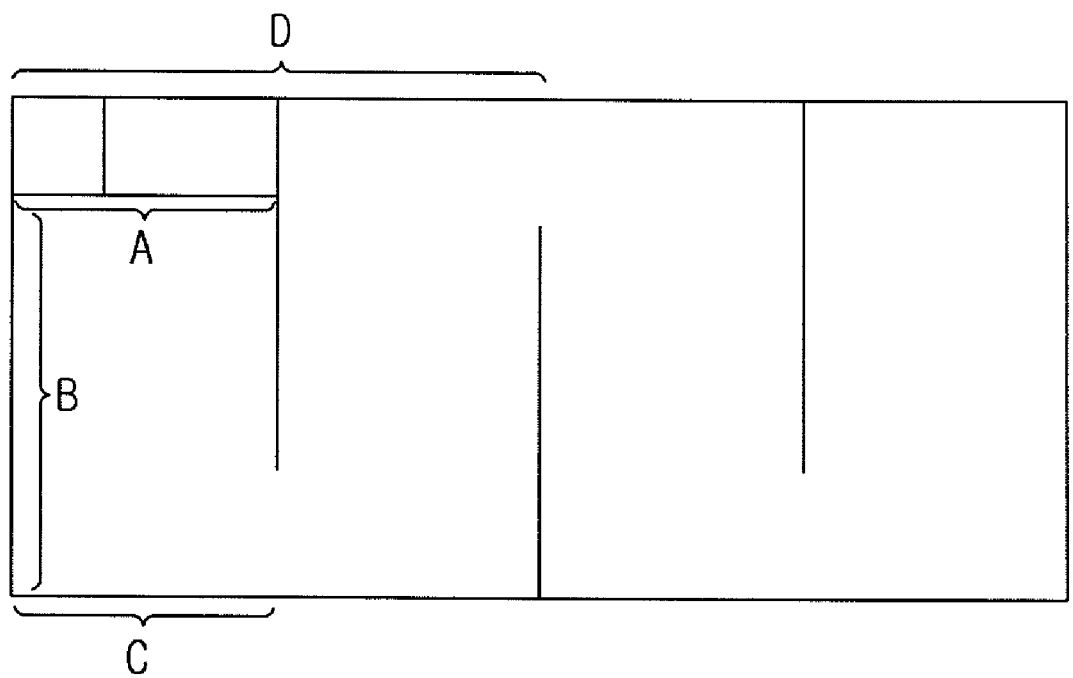
FIG. 4 is a top view schematically illustrating observation sections dividing an apartment-type anaerobic digestion reactor according to the present invention.

According to one aspect of embodiments of the present invention, the anaerobic digestion reactor includes a subsequent treatment reactor in the upper layer (See FIG. 3). The subsequent treatment reactor is divided into a first region 11, a second region 12, a third region 13, and a fourth region 14 and has a structure in which the regions are divided each other by separation walls in the same form of the separation walls 5', 6', and 7' installed in the first region 5, second region 6, third region 7, and fourth region 8 of the anaerobic digestion reactor in the lower layer. The treatment reactor also includes a diffusing gas supply tube (not shown) and a diffuser (not shown) in the same form of those in the lower layer.

In each region 11, 12, 13, and 14 of the subsequent treatment reactor, external air including oxygen is supplied through a brewer (not shown) to a diffusing gas supply tube and a diffuser, and the air sprayed through the diffuser gives the fluidity to an inflow in each region to be transferred in a first-in and first out order. This means that the treatment reactor is operated in the same manner as the anaerobic digestion reactor in the lower layer except that external air is used as a diffusing gas.

In order to remove odor components generated by a final fermentation broth (sludge liquid) of the anaerobic digestion reactor, regions 11, 12, 13, and 14 of the subsequent treatment reactor may be connected to an odor component removal device which purifies and emits a gas produced from an upper gas layer of the regions 11, 12, 13, and 14 externally (See FIG. 1).

As the odor component removal device, an open type B tank may be alone connected to a gas layer of the subsequent treatment reactor for use. The B-type tank includes water containing a *Thiocapsa roseopersicina* culture, dissolves gas drawn in from a gas layer in each region of the subsequent treatment reactor in the water by using a diffuser in the removal device, removes ammonia and hydrogen sulfide as odor components in the form of ammonium sulfate or sulfate salt, and then emits the gas from which the odor components have been removed into the air.

Subsequently, a final fermentation broth in which odor components have been removed may be transferred to a liquid-composting reactor and used as a fertilizer for application to arable land.

Hereinafter, the operating state of an anaerobic digester having the structure will be described with reference to FIG. 1.

An inflow such as livestock wastewater, food waste, etc. is introduced into a first input reactor and warmed by heat from a heat exchange pipe (a first heat exchange pipe) included in the first input reactor. The inflow whose heat exchange has been completed to be warmed is overflown into a second input reactor, introduced into a first region of the anaerobic digestion reactor in the lower layer, and passes through a second region, a third region, and a fourth region of the anaerobic digestion reactor in sequence in a first-in and first-out manner. As a result of an anaerobic digestion, biogas is produced and stored in the upper portion of each region. In the side wall of the first region of the anaerobic digestion reactor, a heat exchange pipe (a second heat exchange pipe) in which an engine exhaust gas or a boiler flue gas supplied from an external waste heat gas supply device may be circulated is included to minimize a variation between the temperatures of the inflow and the optimal anaerobic digestion. A floor-heating piping which is installed on the floor from the first region to the fourth region supplies heat to the inflow in order to achieve the same purpose.

A diffusing gas supply tube and a diffuser are installed on the floor of the first, second, third, and fourth regions of the anaerobic digestion reactor, stir the inflow passing through each region, and provide fluidity to the inflow. The gas draws in a biogas in the upper portion of the second and fourth regions through an external brewer, and ammonia and hydrogen sulfide included in the biogas are supplied to the diffusing gas supply tube and the diffuser from the first region to the fourth region with or without removal of the ammonia and hydrogen sulfide. The biogas which does not pass through the ammonia and hydrogen sulfide removal device is usually transferred to a diffusing gas supply tube, a diffuser, and a diffusing gas separation wall in the first region, and as a result, the lowered pH value of the inflow in the first region by performing an acid production step will satisfy pH conditions of the inflow appropriate for the next region to perform methane fermentation with the help of stirring and fluidity by providing the biogas including ammonia. The biogas passing through the ammonia and hydrogen sulfide removal device is usually supplied to the third to fourth regions, and as a result, a high-purity biogas in which ammonia and hydrogen sulfide are maximally removed is accumulated in a gas layer of the fourth region, in which a final biogas is stored. If necessary, the accumulated biogas may pass through a hydrogen sulfide removal device to be used as a fuel for electricity generation/heat production in the state that almost all the residual hydrogen is removed.

A final fermentation broth (sludge liquid) which reaches the fourth region of the anaerobic digestion reactor and completes the anaerobic digestion is collected in the lower portion of the fourth region. The final fermentation broth is drawn in through an inlet pipe in the lower portion, transferred to a first heat exchange pipe included in a first input reactor, and moved into a subsequent treatment reactor in an upper layer of the anaerobic digestion reactor after heat generated as a result of a final fermentation is provided to a new inflow to be introduced. Activated liquid is present in the upper layer portion of the fourth region of the anaerobic digestion reactor except for a final fermentation broth in the lower layer. Some of the liquid is supplied through an inlet pipe in the upper layer portion to a second input reactor and used as a liquid inoculum and a pH adjusting liquid, and the other is used as a diluent for livestock wastewater or food waste to be introduced into a first input reactor.

The final fermentation broth (sludge liquid) transferred to a subsequent treatment reactor in the upper layer of the anaerobic digestion reactor moves in a first-in and first out manner into first, second, third, and fourth regions of the subsequent treatment reactor having the same structure as the first, second, third, and fourth regions of the anaerobic digestion reactor in the lower layer. The process for providing stirring and fluidity to the final fermentation broth is performed in the same manner as in the anaerobic digestion reactor. However, external air including oxygen is injected into the diffusing gas supplied through a diffusing air supply tube and a diffuser unlike the anaerobic digestion reactor. The final fermentation broth moving into each region of the subsequent treatment reactor generates odor components such as ammonia, hydrogen sulfide, etc. to a gas layer in the upper portion, and these odor components are again transferred to the ammonia and hydrogen sulfide removal device to be removed and externally emitted. The final residual fermentation broth is transferred to a liquid-composting reactor and used as a fertilizer for application to arable land, thereby completing an anaerobic digestion process through an anaerobic digester according to the present invention.

Because a gas layer in the upper portion of the anaerobic digestion reactor serves as a gas storage unit as well in the anaerobic digester according to the present invention, a separate gas storage unit is not required. The water level of an input reactor may be also controlled by gas pressure in a gas layer, and the operation of an additional apparatus such as an engine for electricity generation connected to the anaerobic digestion reactor may be controlled through a digestion liquid level measurement tube.

In the anaerobic digester according to the present invention, the oxidation and reduction potential (ORP) of the first and fourth regions of the anaerobic digestion reactor is measured at −330 mV to −460 mV, respectively, satisfying bacteria culture conditions of anaerobic digestion reactors requiring −300 mV or less.

Furthermore, the anaerobic digester according to the present invention does not require pretreatment when an inflow is introduced and provides optimal conditions for growth and development of methanogen by controlling the temperature of the inflow throughout the whole process including an initial input step, an anaerobic digestion step, etc. using waste heat.

When unfermented liquid which is subsequently introduced is firstly out, the anaerobic digester according to the present invention may remove factors which may deteriorate the removal efficiency of odor components in the subsequent treatment by allowing the inflow to move in a first-in and first-out manner.

Furthermore, the anaerobic digester according to the present invention does not require a separate stirring unit inside the anaerobic digestion reactor and may slowly transfer the inflow such that floatation and homogenization of deposits in the inflow may be induced with or without purification of a self-produced biogas for recycling.

In addition, the anaerobic digester according to the present invention may draw in biogas from a gas layer in the anaerobic digestion reactor and recirculate it through an ammonia and hydrogen sulfide removal device to produce a high-purity biogas. Through the removal device, a sustained concentration of ammonia and hydrogen sulfide, which has been identified as a disadvantage of conventional gas stirring-type anaerobic digestion reactors and inhibits the growth and development of methanogen, may be prevented.

Furthermore, when it is a combined A-type and B-type tank 28, the ammonia and hydrogen sulfide removal device according to the present invention may remove 99% or more of ammonia and 30% or more of hydrogen sulfide to be produced, and a removal device 28' which is connected to the combined removal device 28 and includes iron hydroxide (II) or iron hydroxide (III) may remove 99% or more of hydrogen sulfide produced by increasing the passing frequency into the removal device.

In addition, the ammonia and hydrogen sulfide removal device 28 according to the present invention may consume carbon dioxide, when an enzyme produced in a *Thiocapsa roseopersicina* culture included therein removes hydrogen sulfide, to decrease carbon dioxide content in biogas primarily. Furthermore, residual carbon dioxide and hydrogen in biogas as described above may be provided as a substrate for methanogen in the digestion liquid to convert carbon dioxide as an impurity into methane and decrease the carbon dioxide content secondarily. Conventional anaerobic digestion reactors for biogas production only contain 65% or less of methane and 35% or more of carbon dioxide. However, the removal device according to the present invention may be used in the anaerobic digestion reactor to produce biogas whose methane content is 80% or more, the level of municipal gas, by lowering carbon dioxide content in the biogas to 20% or less (See FIG. 2).

TABLE 2

| Measurement | $H_2S$ (ppm) | | $CO_2$ (%) | | $NH_3$ (ppm) | | Passing frequency into a removal device |
|---|---|---|---|---|---|---|---|
| | Measurement position 1 | Measurement position 2 | Measurement position 1 | Measurement position 2 | Measurement position 1 | Measurement position 2 | |
| 1 | 5000 | 1600 | 23 | 18 | 25 | — | 1 |
| 2 | 1600 | 320 | 20 | 17 | 25 | — | 2 |
| 3 | 600 | 40 | 20 | 18 | 40 | — | 3 |

Table 2 is a measurement result of the removal efficiency of ammonia, hydrogen sulfide, and carbon dioxide by a removal device according to the present invention. Specifically, Table 2 is a result of the ingredient and content of a biogas measured at a GASTEC Detector (manufacturer: Japan) tube (measurement position 1) between a brewer 29 and an A-type tank in FIG. 12 (*a*) by increasing the passing frequency into the removal device from 1 to 3, and measured at a position (measurement position 2) out of the A'-type tank of the removal device 28' in FIG. 12 (*a*). Referring to Table 2, ammonia was fully removed only by an initial one time passing while about 68%, about 80%, and about 94% of hydrogen sulfide was removed by one, two, and three passing frequencies, respectively. It can be seen that carbon dioxide may be included at 20% or less in biogas and a high-purity biogas may be produced from an anaerobic digestion reactor including a removal device according to the present invention.

It is apparent to those skilled in the art to which the present invention pertains that various modifications and changes can be made without departing the spirit and scope of the present invention and all these modifications and changes are intended to be contained with the accompanying claims.

For example, an anaerobic digester according to the present invention includes an anaerobic digester which has structures of a monolayer type with an upper layer and a lower layer separated as well as of a double layer of an upper layer and a lower layer described in the Detailed Description and Claims, and technical features of the upper layer and the lower layer embodied in one monolayer. The ammonia and hydrogen sulfide removal device 28 or hydrogen sulfide removal device 28' according to the present invention is not limited to the use only for the anaerobic digester according to the present invention. Rather, the removal device 28 or the removal device 28' may be appropriately modified according to the structure of the device as long as it is a device provided for the purpose of removing gasses such as ammonia, hydrogen sulfide, carbon dioxide, etc, and obtaining a high-purity biogas. Furthermore, it may be applied to a device for removing sulfur, ammonia, carbon dioxide, etc, as well as a device for producing biogas.

What is claimed is:

1. A rectangular-shaped anaerobic digester, comprising:
a first input reactor into which livestock wastewater or food waste (hereinafter, 'inflow') is introduced;
a second input reactor into which the inflow passing through the first input reactor is introduced;
first, second, third, and fourth regions of an anaerobic digestion reactor designed for the inflow passing through the second input reactor to perform methane fermentation in a first-in and first-out order to produce and transfer biogas simultaneously into the next anaerobic digestion region;
a diffusing gas supply tube and a diffuser giving fluidity to the inflow of the first, second, third, and fourth regions;
an inlet pipe in a lower layer portion of the fourth region of the anaerobic digestion reactor, into which sludge liquid is drawn in from the lower layer portion;
an inlet pipe in an upper layer portion of the forth region of the anaerobic digestion reactor, into which activated liquid is drawn in from the upper layer portion;
a biogas capturing device which is connected to a gas layer in the fourth region of the anaerobic digestion reactor;
a first heat exchange tube provided inside the first input reactor to allow the sludge liquid drawn in from the inlet pipe in the lower layer portion to perform heat exchange with a new inflow;
first, second, third, and fourth regions of a subsequent treatment reactor provided on the upper layer of the anaerobic digestion reactor, to allow the sludge liquid whose heat exchange is completed to be introduced in a first-in and first-out order, and to treat gas odor components generated from the sludge liquid; and
a liquid-composting reactor in which an emitted sludge whose odor components have been removed is stored.

2. The digester as set forth in claim 1, wherein the floor of the first, second, third, and fourth regions of the anaerobic digestion reactor comprises a floor-heating piping to maintain a temperature for methane fermentation.

3. The digester as set forth in claim 1, wherein each region of the anaerobic digestion reactor has a structure in which a space for storing biogas produced by methane fermentation is secured.

4. The digester as set forth in claim 1, wherein each region of the anaerobic digestion reactor has a structure in which the regions are divided each other by separation walls, in each of which the terminal portion is opened in the form of the ']', and the inflow and biogas move through the open space into the next region.

5. The digester as set forth in claim 4, wherein the separation wall of each region of the anaerobic digestion reactor has a structure in which a separation wall between a first region and a second region and a separation wall between a third region and a fourth region are opened in the same direction, a separation wall between the second region and the third region is opened in the direction opposite to the openings of the separation wall between the first region and the second region and the separation wall between the third region and the fourth region, and an inflow moves in a zig-zag manner throughout the whole regions of the anaerobic digestion reactor.

6. The digester as set forth in claim 1, wherein the diffusing gas supply tube and the diffuser include a diffusing gas supply tube and a diffuser in a first region and a second region provided around the perimeter of a wall on the floor of a side wall in the direction of the second region of a separation wall installed between the second and a third regions, on the floor of an inner side wall from the first region to the second region, which is vertical to the separation wall, and on the floor of an inner side wall in the first region, which is vertical to an inner side wall from the first region to the second region, and a diffusing gas supply tube and a diffuser in a third and a fourth region provided around the perimeter of a wall on the floor of a side wall in the direction of the third region of a separation wall installed between the second and the third regions, on the floor of an inner side wall from the third region to the fourth region, which is vertical to the separation wall, and on the floor of an inner side wall in the fourth region, which is vertical to an inner side wall from the third region to the fourth region.

7. The digester as set forth in claim 1, wherein the first region of the anaerobic digestion reactor has a second heat exchange tube which is formed on the surface of the side wall opposite to a separation wall in the first region and may exchange a heat supplied from an external source to maximize the methane fermentation efficiency by minimizing a temperature variation between the temperature of initially introduced inflow and the optimal fermentation temperature for methanogenesis.

8. The digester as set forth in claim 7, wherein the heat supplied form the external source is a waste heat produced by a boiler flue gas or an engine exhaust gas.

9. The digester as set forth in claim 7, wherein the first region of the anaerobic digestion reactor has a diffusing gas partition wall in front of the second heat exchange tube and a diffusing gas supply tube and a diffuser are installed on the floor between the wall on which the second heat exchanger is installed and the diffusing gas partition wall, and wherein the diffusing gas partition wall induces the flow of the diffusing gas exiting from the diffuser in the vertical direction, and then allows the diffusing gas passing through the diffusing gas partition wall to provide clockwise fluidity to the inflow passing through the first region.

10. The digester as set forth in claim 1, wherein the second region of the anaerobic digestion reactor comprises a gas piping to recover a gas produced as a result of anaerobic digestion and supply the gas to a diffusing gas supply tube and a diffuser in the first region and the second region, provided around the perimeter of a wall on the floor of a side wall in the direction of the second region of a separation wall installed between the second and the third regions, on the floor of an inner side wall from the first region to the second region, which is vertical to the separation wall, and on the floor of an inner side wall in the first region, which is vertical to an inner side wall from the first region to the second region, and wherein the fourth region of the anaerobic digestion reactor comprises a gas piping to recover a gas produced as a result of anaerobic digestion and supply the gas to a diffusing gas supply tube and a diffuser in the third region and the fourth region provided around the perimeter of a wall on the floor of a side wall in the direction of the third region of a separation wall installed between the second and the third regions, on the floor of an inner side wall from the third region to the fourth region, which is vertical to the separation wall, and on the floor of an inner side wall in the fourth region, which is vertical to an inner side wall from the third region to the fourth region.

11. The digester as set forth in claim 10, wherein the gas piping comprised in the fourth region of the anaerobic digestion reactor is connected to a device for removing ammonia and hydrogen sulfide comprised in a gas produced as a result of anaerobic digestion and supplies a gas with ammonia and hydrogen sulfide removed to a diffusing gas supply tube and a diffuser comprised in the third region and the fourth region to maintain an optimal pH for methane fermentation and increase the purity of a biogas finally produced.

12. The digester as set forth in claim 10, wherein the gas piping comprised in the second region of the anaerobic digestion reactor is connected to a gas piping comprised in the fourth region of the anaerobic digestion reactor, into which a gas passing through an ammonia and hydrogen sulfide removal device moves, and selectively supplies or blocks the gas with ammonia and hydrogen sulfide removed to a diffusing gas supply tube and a diffuser comprised in the first and second regions.

13. The digester as set forth in claim 11, wherein the ammonia and hydrogen removal device comprises a closed-type tank (hereinafter, 'A-type tank') comprising:
   a diffuser to which a biogas comprising ammonia and hydrogen sulfide transferred from a gas layer in an anaerobic digestion reactor is supplied;
   water in which the biogas supplied from the diffuser is dissolved;
   a drain pipe through which the water in which the biogas is dissolved is emitted by water level and gas pressure in a lower portion;
   an inlet pipe through which water in which ammonia and hydrogen sulfide is removed is introduced into an upper portion; and
   an exhaust pipe through which the gas with the ammonia and hydrogen sulfide removed is returned to the anaerobic digestion reactor; and
   an open-type tank (hereinafter, 'B-type tank') which comprises a Thiocapsa roseopersicina culture comprising:
   a water pipe through which the water drained from a lower portion of the A-type tank is introduced in an upper portion;
   a ball tap for water level control connected to and supported by the water pipe;
   a level sensor which senses water level;
   a diffuser to which external air is supplied;
   a drain pipe, through which water with ammonia and hydrogen sulfide removed is drained in a lower portion; and
   a drain pump which is connected to the drain pipe and performs an on/off function according to a water level sensing information of the level sensor,
   wherein the A-type tank is connected each other to the B-type tank.

14. The digester as set forth in claim 13, wherein the A-type tank of the ammonia and hydrogen sulfide removal device supplies ammonia and hydrogen sulfide dissolved in water to the B-type tank, in which the ammonia and hydrogen sulfide are reacted with oxygen supplied from the external air, and removes the ammonia and hydrogen sulfide in the form of ammonium sulfate $((NH_4)_2SO_4)$.

15. The digester as set forth in claim 13, wherein the B-type tank of the ammonia and hydrogen sulfide removal device uses a Thiocapsa roseopersicina culture to remove carbon dioxide or hydrogen sulfide in the biogas in the form of formaldehyde $(CH_2O)$, sulfuric acid $(H_2SO_4)$ salt or pure sulfur (S).

16. The digester as set forth in claim 13, wherein the B-type tank of the ammonia and hydrogen sulfide removal device is supplied with oxygen dissolved in water from the external air to block the oxygen input into the anaerobic digestion reactor.

17. The digester as set forth in claim 13, wherein a level sensor in the B-type tank of the ammonia and hydrogen sulfide removal device comprises three sensor rods which are different each other in length, operates a drain pump to supply water with ammonia and hydrogen sulfide removed to the A-type tank when the water level of the B-type tank touches the shortest sensor rod, and stops the operation of the drain pump when the water level of the B-type tank touches the middle-length sensor rod to perform a removal reaction of the ammonia and hydrogen sulfide.

18. The digester as set forth in claim 13, wherein the ammonia and hydrogen removal device transfers a dissolved biogas with ammonia and hydrogen sulfide removed through the B-type tank to the A-type tank and supplies it through an exhaust pipe in an upper portion of the A-type tank to a diffusing gas supply tube and a diffuser in the lower portion.

19. The digester as set forth in claim 13, wherein the ammonia and hydrogen sulfide removal device dissolves a biogas with ammonia and hydrogen sulfide removed through a diffuser in the upper portion of the A-type tank and further connects a hydrogen sulfide removal device which removes a residual hydrogen sulfide in the form of iron sulfide and water by reacting iron hydroxide (II) or iron hydroxide (III) with the residual hydrogen sulfide to the A-type tank, in order to increase the removal efficiency of hydrogen sulfide.

20. The digester as set forth in claim 19, wherein the hydrogen sulfide removal device is a closed type tank ("A type tank"), comprising: an inlet pipe into which a biogas with some hydrogen sulfide removed is introduced through the ammonia and hydrogen sulfide removal device of claim 13; a diffuser which diffuses the biogas introduced from the inlet pipe; water comprising iron hydroxide (II) or iron hydroxide (III) reacting with hydrogen sulfide in the biogas supplied from the diffuser; and an exhaust pipe which emits a biogas with hydrogen sulfide removed.

21. The digester as set forth in claim 1, wherein a sludge liquid which is drawn into an inlet pipe in the lower portion of the fourth region of the anaerobic digestion reactor provides heat generated as a result of a temperature increase by anaerobic digestion to a new inflow while being circulated in a first heat exchange tube of the first input reactor and minimizes a temperature variation between the temperatures of an optimal methane fermentation and the new inflow.

22. The digester as set forth in claim 1, wherein some of the activated liquid which is drawn into an inlet pipe in the upper layer portion of the anaerobic digestion reactor is introduced into a second input reactor and used as a liquid inoculum when an inflow is a livestock wastewater.

23. The digester as set forth in claim 1, wherein some of the activated liquid which is drawn into an inlet pipe in the upper layer portion is used for dilution according to the concentrations of the inflow before the inflow is introduced into a first input reactor.

24. The digester as set forth in claim 1, wherein in order to increase the removal efficiency of hydrogen sulfide, between a biogas layer of the fourth region of the anaerobic digestion reactor and a biogas capturing device connected thereto, a hydrogen sulfide removal device is comprised to supply a biogas from the biogas layer through a diffuser in the tank comprising water into which iron hydroxide (II) or iron hydroxide (III) is added and to be reacted with a residual hydrogen sulfide in the biogas to remove the residual hydrogen sulfide in the form of iron sulfide.

25. The digester as set forth in claim 1, wherein a first region, a second region, a third region, and a fourth region of a subsequent treatment reactor comprised in the upper layer of the anaerobic digestion reactor are divided each other by separation walls in the same form of the separation walls installed in the first region, second region, third region, and fourth region of the anaerobic digestion reactor in the lower layer and comprise a diffusing gas supply tube and a diffuser in the same form.

26. The digester as set forth in claim 25, wherein an external air comprising oxygen is supplied through a brewer to a diffusing gas supply tube and a diffuse in each region of the subsequent treatment reactor, and the air sprayed through the diffuser gives the fluidity to an inflow in each region to be transferred in a first-in and first out order.

27. The digester as set forth in claim 25, wherein each region of the subsequent treatment reactor is connected to an odor component removal device which purifies and emits a gas produced in an upper gas layer of each region externally in order to remove odor components generated from the inflow.

28. The digester as set forth in claim 25, wherein the odor component removal device is an open-type tank which comprises water containing a Thiocapsa roseopersicina culture, dissolves a gas drawn in from a gas layer of each region in the subsequent treatment reactor through a diffuser in the removal device into the water to remove ammonia and hydrogen sulfide as a odor component in the form of ammonium sulfate or sulfuric acid salt, and then emits the gas with odor components removed into the air.

* * * * *